(12) United States Patent
Mahajan et al.

(10) Patent No.: US 8,890,701 B2
(45) Date of Patent: Nov. 18, 2014

(54) INSET DUCT CARBON MONOXIDE MONITOR-DETECTION SYSTEM

(76) Inventors: Kamal Mahajan, Greenlawn, NY (US); Ron Lissack, Great Neck, NY (US)

( * ) Notice: Subject to any disclaimer, the term of this patent is extended or adjusted under 35 U.S.C. 154(b) by 207 days.

(21) Appl. No.: 13/229,910

(22) Filed: Sep. 12, 2011

(65) Prior Publication Data

US 2013/0063270 A1    Mar. 14, 2013

(51) Int. Cl.
*G01N 30/32* (2006.01)
*G08B 21/14* (2006.01)
*G01N 35/00* (2006.01)
*G01N 33/00* (2006.01)
*G08B 29/18* (2006.01)
*G01N 30/38* (2006.01)

(52) U.S. Cl.
CPC .......... *G08B 21/14* (2013.01); *G01N 35/00871* (2013.01); *G01N 33/004* (2013.01); *G01N 30/32* (2013.01); *G01N 33/0063* (2013.01); *G08B 29/183* (2013.01); *G01N 2030/385* (2013.01); *G01N 2030/324* (2013.01)
USPC .............................. 340/632; 340/628; 702/23

(58) Field of Classification Search
CPC . G01N 33/004; G01N 30/32; G01N 33/0063; G01N 35/00871; G01N 2030/324; G08B 21/14; G08B 29/183
USPC ...................................... 340/628, 632; 702/23
See application file for complete search history.

(56) References Cited

U.S. PATENT DOCUMENTS

| | | | |
|---|---|---|---|
| 7,687,748 B2 * | 3/2010 | Gagas | 219/623 |
| 8,106,785 B2 * | 1/2012 | Yokota | 340/628 |
| 8,341,936 B2 * | 1/2013 | Zhang | 60/276 |
| 2009/0308134 A1 * | 12/2009 | Pepper | 73/1.06 |
| 2010/0201531 A1 * | 8/2010 | Pakravan et al. | 340/632 |

* cited by examiner

*Primary Examiner* — Daniel Wu
*Assistant Examiner* — Benyam Haile
(74) *Attorney, Agent, or Firm* — Bernard S. Hoffman

(57) ABSTRACT

A toxic gas detector including ductwork, an enclosure, and a toxic gas sensor. The ductwork communicates with a heating source of a forced hot air heating system. The enclosure is attached directly to, and communicates with, the ductwork, and is disposed directly adjacent to the heating source. The toxic gas sensor is disposed in the enclosure, communicates with the ductwork, and is disposed directly adjacent to the heating source so as to allow the toxic gas sensor to detect a toxic gas at the heating source before the toxic gas has a chance to be distributed through the ductwork and infiltrate all outlets of the ductwork, and when the toxic gas sensor detects the toxic gas at the heating source, the toxic gas detector automatically shuts down the heating source.

41 Claims, 10 Drawing Sheets

INSET DUCT CARBON MONOXIDE MONITOR-DETECTION SYSTEM

FIELD OF THE INVENTION

The present invention relates to; and is classified as a microcontroller based carbon monoxide detection and annunciation system. In the general field of carbon monoxide detection, primarily for consumer usage, prior art maintains the general concept of small portable and mostly economical devices that usually are placed throughout a consumer's home or place of business. The reliability of said prior art is dependent upon the care and strategy in the initial placement of said detectors. The future safety of the consumer depends on whether the devices are periodically maintained. Even though current CO detector systems remains simple in design, it is this factor that is the inherent problem associated with the prior art. Another factor limiting the effectiveness of this prior art is that detector placement is from room to room, and the area covered can have fringe spots. Fringe spots are areas within a household or business, where the detection of carbon monoxide is greatly compromised due to nonuniform distribution of the toxic carbon monoxide as it permeates from the source. That prime source is the furnace burner mechanism. Current prior art omits this problem of toxic gaseous nonuniform distribution, emanating from a burner source, in product design. Another important potential problem that arises with current prior art is the compromise of response time for annunciation. The permeation of carbon monoxide, once chemically generated from the following:

Faulty furnace burner ignition, carbonized soot accumulation, or blocked flue flow due to external causes such as physical damage to the flue system, exists as a life threatening condition that usually allows for only minutes to be detected and dealt with properly. Where life is concerned, any delay in annunciation is rendered deadly and life threatening.

High or Low in a Room

It makes no difference where you put the detector but not because carbon monoxide and air have approximately the same density. Both are gases and as a result, diffusion alone and the entropy effect will take care of mixing them. Any convection currents and/or forced-air turbulence present will also enable the gases to mix and affect the detector.

It is popularly misconceived that light (low-density) gases will somehow float atop heavy (higher density) gases. Indeed, if the higher density gas was admitted low in the room, and done so in a manner that would not cause much mixing, it would take a while for the gases to become thoroughly mixed by the mechanisms mentioned above. Even so, they would eventually mix.

That said, since time to detection is of the essence, and in circumstances where the contaminant gas (such as radon—a gas of very high density) gets into the room through entry points more or less at floor level, where one puts the detector can become important.

The density of a gas is proportional to the weight of a single molecule of that gas.

Calculating relative buoyancy starts by learning a few atomic weights:
H=1, He=4, C=12, N=14, O=16.
  Summation for the molecular weights of pure gasses:
  H2=(1+1)=2, very light
  He=(4)=4, very light
  N2=(14+14)=28, about neutral
  O2=(16+16)=32, slightly heavy
  CO2=(12+16+16)=44, heavy
  CO=(12+16)=28, about neutral
  CH4=(12+4*1)=18, light (majority part of natural gas)
  H2O=(2*1+16)=18, light (steam)
  C2H6=(2*12+6*1)=30, about neutral (minority part of natural gas)
  C3H8=(8+3*12)=42, heavy (propane)
  C4H10=(10+4*12)=58, (butane)
  C5H12=(12+5*12)=70, pentane, lightest part of gasoline
  For mixed gasses just take a proportionate average:
Air is 80% N2+20% O2.
  air=0.8(28)+0.2(32)=29 (exactly neutral, by definition)
  So pure carbon monoxide is actually about 3% lighter than air.
  But usually it is made in modest concentrations, mixed in with the normal so combustion products: CO2, H2O.
  Which are always mixed with the 80% Nitrogen that never participates in burning.
  Then that mixes with room air, making an even smaller concentration . . . .
  And there are uncertainties . . . .
  Some fuels make light exhaust (more H2O), some make heavy (more CO2).
  Then when the exhaust cools the light part, H20 (steam), may condense and drop out.
  Not to mention that the exhaust gas was expanded when hot, and it contracts as it cools.
  No rule can predict which way it is going to go in most circumstances, however Brownian Movement is a major influencing factor.
  Because it travels in whatever directions your air normally circulates, which varies, it is difficult in most homes to find an advantageous position where CO will enter or concentrate. So consumers settle for any convenient position, or one associated with, which they wish to protect, namely themselves, breathing in air at medium heights.
  Doing a really good job of CO detection needs more than one detector, but CO detectors are not cheap enough for that yet.
  The general rule is one for each potential source of carbon monoxide or area where carbon monoxide can accumulate, plus one for each protectee is usually the rule or suggestion.
  National Fire Protection Association has a code, number 720, 2-1.1.2* 1998 states that: "A carbon monoxide alarm or detector should be centrally located outside of each separated sleeping area in the immediate vicinity of the bedrooms. Where bedrooms are separated and the audibility of the alarm or detector to occupants within the bedroom area could be seriously impaired, more than one unit could be needed. Each alarm or detector should be located on the wall, ceiling, or other location as specified in the installation instructions that accompany the unit."
  In addition more than CO will be emitted with furnace failure or with the use of unvented heaters. Carbon dioxide a heavier gas will collect on the floor building up and possibly preventing carbon monoxide from ever reaching the alarm if located at a floor outlet. That is why it is recommended that CO alarms be placed high around eye level where the higher concentrations would be concentrated.
  At best, any prediction for concentrations of large volumes of gases, such as rooms, can be estimated using Monte Carlo Integration techniques, which are the basis of most predictive algorithms in practice and held as tantamount effective predictive analysis.
  Picking N randomly distributed points $x_1, x_2, \ldots, x_n$ in a multidimensional volume V to determine the integral of a function f in this volume gives a result $$\int f dV \approx V(f) \mp \frac{\sqrt{\langle f^2 \rangle - \langle f \rangle^2}}{N}$$

$$\frac{1}{N}\sum_{i=1}^{N} f(x_i)$$

$$\frac{1}{N}\sum_{i=1}^{N} f^2(x_i)$$

Carbon Monoxide Alarms (New York State Law)

New Carbon Monoxide Detector Law Affects All Homes

New CO Law—"Amanda's Law" goes into effect Feb. 22, 2010_Amanda's Law is named after Amanda Hansen. The 16-year-old West Seneca, N.Y., girl died of carbon monoxide poisoning on Jan. 17, 2009, while at a sleepover at a friend's home. A malfunctioning boiler that emitted carbon monoxide is the probable cause of her death. This law changes the requirements of location and the number of detectors needed in residential occupancies in New York State, both existing and new construction that have an appliance, device, or any type of source that may emit carbon monoxide. This law requires you to have a carbon monoxide detector within each dwelling unit or sleeping unit where a carbon monoxide source is located. There are different regulations depending on the date of construction. Below is an excerpt of the law, complete text can be found at http://www.dos.state.ny.us/CODE/COAlarm.htm Carbon monoxide alarms. This section covers the installation, performance and maintenance of carbon monoxide alarms and their components in new and existing buildings. The requirements of this section shall apply to all new and all existing buildings, without regard to the date of construction of the building and without regard to whether such building shall or shall not have been offered for sale.

Exception: Compliance with this section is not required where no carbon monoxide source is located within or attached to the structure. However, compliance with this section is required if any carbon monoxide source is subsequently located within or attached to the structure.

BACKGROUND OF THE INVENTION

The present invention teaches that a novel alternative approach to the distribution of multi-detector placement throughout a home or edifice can be simplified and reduced in the number of detectors required. The reduction can practically be reduced to the actual number of heater/boilers in place within the confines of said home or edifice, i.e. one heater/boiler yields one novel detector of said present invention.

With current prior art, the number and placement of carbon monoxide detectors remains a tedious and costly venture and the effectiveness of the outcome depends on the installation. If the installation is in question, then the risks are with the safety of the consumer. The present invention offers a microcontroller based method means for completely controlling the periodic and constant interrogation for the presence of carbon monoxide at the source of the carbon monoxide, which is from the burner itself. With current prior art, all of the detection method means is for placement of individual CO detectors, by best "guess-estimate" techniques. With the current prior art, placing various CO detectors throughout a home or edifice can be problematic because determining position and accessibility for maintenance varies from room to room. Not taking care in the initial installation compromises the effectiveness of said CO detectors in place. With prior art CO detectors, capturing a sample of the ambient air for each room area depends completely on Brownian Movement Dynamics and the quantity or concentration of carbon monoxide at the CO sensor contained within the prior art CO detector means. FIG. 1A is a three dimensional graphic representation of Brownian Movement Dynamics, which shows the pseudo-random distribution of carbon monoxide, other extraneous gases and dust particles. The dynamics of this movement varies greatly from room to room and other factors involved in said movement such as temperature, extraneous convection currents of air, and room size are all contribute to the complexity. Striking as it may seem, all prior art omits the advantageous solution of considering the actual potential source of carbon monoxide in a home or edifice that has a centralized heating system, as a place of detection means. That source is the heating system itself. Quite fundamental, yet ignored by current prior art method means. Ergo, the novelty and intention of the present invention is for placing the carbon dioxide detection method means as close to the burner or boiler as possible. For it should be obvious to anyone steeped in the art, that the burner or boiler is the prime source of carbon monoxide that is mixed with the hot air and distributed, by way a circulating duct means, to all rooms throughout a home or edifice. It should further be obvious to anyone steeped in the art that if a carbon monoxide detector method means of the present invention is placed at said burner or boiler source, the effectiveness and "assured safety" associated with the present invention CO detector method means is optimized. Another intention of the present invention is for the instant furnace burner or boiler heater shut down and annunciate to all occupants that carbon monoxide is detected. Another feature of the present invention is its wireless feature that can send wireless data to remote receivers, such as personal computers incorporated into a more complex scheme for home or commercial use. Further it should be obvious to anyone steeped in the art that the present invention, being required to have its placement at the burner or boiler source, reduces the number of prior art room CO detectors to zero. The present invention is the only method means necessary for an optimized CO detection system. This reduces the cost and complexity of a CO detection system greatly, which is another intention of the present invention. The cost factor advantage of the present invention versus that of current prior art, is further enhanced and understood by the following comparison:

| Current Prior Art | The Present Invention |
| --- | --- |
| Requires a CO detector for each room. | Requires only one CO detector at burner or boiler source. |
| Placement of each detector can be problematic. | Uses a novel means of placement nearest to the burner or boiler. |

-continued

| Current Prior Art | The Present Invention |
| --- | --- |
| Depends on Brownian Movement for detection for obtaining samples to contact the CO sensor. Highly dependent on room dynamics, relating to air flow. | Uses a novel means for instantly capturing air samples from the heater source via duct-work and sends the sample to the internal sensor by a fan means. |
| Uses simple pass by means for detection and annunciation. Can encounter delays in detecting carbon monoxide. | Uses a microcontroller to constantly update and interrogate for carbon monoxide presence, and instant annunciation by local or remote means. |
| Power source: The majority use a battery | Power source: power line. (There is no battery because if there is no power, there is no need to monitor as the furnace or the boiler will not generate CO if it does not have power). |
| Annunciation is local to the CO detector in each room. Possible problem of hearing from room to room. | Wireless remote operation. Annunciation is both local and remote via wireless transfer to a personal computer. Can interrogate and sample air from the burner or boiler whether the furnace system duct fan is on or not. |
| Shutting down the furnace is the task of the consumer, if they alerted in time before they are asphyxiated. | Major advantage: Can shut down the furnace burner or boiler instantly upon detection of carbon monoxide. |
| Time delays for shut down. | Shut down: Instant. |
| Average price per prior art CO detector: $55. | Although the price is more than one unit, cost is less than the average price of a prior art installation for a five room home. Non existent safety compromises. |

THEORY OF OPERATION

The distribution and accumulation of carbon monoxide in any home or edifice, sans various convection and forced air currents, by Brownian Movement is illustrated in FIG. 1A. The drift and meandering of gases such as carbon monoxide are complicated to "path predict." This academic endeavor, if pursued, can with favorable success be calculated using Monte Carlo Integration methods. However for any convenient prediction, the "guess-timate" approach of placing prior art room CO detectors. These types of CO detectors remain problematic in that they detect carbon monoxide after the toxic gas has had the opportunity to permeate throughout a household or other edifice. This exists as a condition that leaves the occupants of a given household or edifice in danger of being asphyxiated before alarms trigger. This mainly arises from delays in detecting the gas, alerting occupants, and then hopefully having occupants do the task of shutting off the furnace, before it's too late.

It therefore is the novelty, methodology means, and prime intention of the present invention 100 in FIG. 1 to overcome these limitations, which are potentially life threatening, and remain as safety issues; all inherent in prior art CO detectors.

FIG. 2, shows the physical structure of the present invention and by observation of the cutaway view, the individual components within the enclosure 101 of the present invention of a CO detector are illustrated. The operation of the present invention CO detector system begins with having air 106 sampled from an exterior source and traveling through a vent tube 104, which is inserted in a furnace duct circulation system, closest to the burner or boiler from which the heated air is forced to flow throughout the duct circulation system by a furnace system blower fan. This captured air 106 from the duct, which the CO detector 101 enters the enclosure through the sampling fan means 107, and the air is further guided and directed by fan blades 108 into an internal venturi means 110. The circulated air 9 is focused and projected by a nozzle means 111 to a carbon monoxide integrated circuit sensor means 120 to begin the micro-controlled sequence means of detecting the presence of carbon monoxide contained in the air sample 106, 109 and then if there is presence of CO, the furnace will immediately shut down and further an alarm will annunciate this audible report to all occupants within a home or other edifice.

The presence of heated air flowing throughout the furnace duct system is periodic and this flow exists under control of the furnace system thermostat controls, which determines when to turn the furnace system fan on or off. It is this proposition of operation that warrants the novelty of the present invention to deal effectively with the possibility of duct air being in a dynamic or static state of circulation.

FIG. 3, shows the present invention enclosure 101 installed within the furnace system duct 102 and illustrates duct air flow 105, the plus signs, into the paper. Whether said air flow exists or not, does not represent a problem for said present invention because of its novelty in using a sample fan 107 to insure that air samples are present when called for by the microcontroller circuit 124. Said captured air 106, is focused at said nozzle 111 and projected onto said CO sensor means 120 and said sensor means 120 signal is translated by said interface circuit 123 and sent to said microcontroller circuit 124. Parameter adjustments for various CO detector 101 can entered at said input control face 113. Various readings from said microcontroller circuit 124 can be viewed at display face 117. FIG. 4, shows said air input tube 104 and its entry opening for duct air samples with a cutaway 106c.

Another novelty of said present CO detector invention 100 in FIG. 1 is how it is easily installed using side mounting tabs 1m and incorporated into a typical furnace duct section 102, as shown in FIG. 5. Said installation is accomplished by cutting out a small circular hole (1 inch diameter or less), inserting the air collector tube 104 with its right angle elbow extension 121 through said small circular hole and then attaching the CO detector unit 101 to the duct-work side plane by screwing the unit to said duct-work side by way of mounting tabs 101m.

Said right angle elbow extension 121, is rotatable at the neck connexion 122 and has the freedom to be rotated 360 degrees; to accommodate any position that will effectively collect the maximum amount of air sample emanating from said duct-work for analysis by the present invention's CO sensor, circuitry, and algorithms. Said present invention's power is obtained from the power mains; once installed and set up for a consumer's specifics, the algorithm takes over being the ever present monitor for toxic carbon monoxide in any home or edifice.

Any typical forced-air furnace duct-work system is analyzed as a complex venturi example. For the purpose of showing a partial of the present invention's novelty, there are three analytical points of interest, as best described in FIG. 7, where $p_d$ (180), $p_i$ (190), and $p_o$ (200) are duct-work pressure at a given point in a(i,k,j) reference space, where (I,k,j) are the unit vectors: I=(1,0,0), k=(0,1,0), and j=(0,0,1) in any (x,y,x) three dimensional coordinate vector space and a=a specific position multiplier vector in said three dimensional coordinate vector space. With the venturi principle applied, if there is a certain value of air pressure $p_d$ (180) in duct-work 102, established by continuous movement of air through said duct-work by a furnace, then any pressure value $p_i$ (190) in sample tube 104, which is at a right angle to said duct-work flow, will be less than that of the average duct-work air pressure $p_d$ (180).

For purposes of teaching the novelty of the present invention, it should be obvious to anyone steeped in the art, that under these conditions, of pressure differential ($p_d$-$p_i$), there will be minimum or no air flow into the internal section of the present invention's enclosure 101 interior and further no sampled air $p_o$ (200) that is required to flow to be in contact with said CO sensor means 120. The underlying physics at play is understood by anyone steeped in the art, to be; that in the immediate vicinity of the opening of said sample tube 104, a(i,k,j) pressure point is represented at the dot product of the duct-work pressure vector $p_d$ (180) and the ambient pressure vector (atmospheric) $p_{at}$. Hence, the scalar value for this pressure dot product is near or at zero when: $(p_d \cdot p_{at}) = |p_d||p_{at}|\cos \theta$, $\theta = 90°$, which is the observed state of a typical flow condition. It should be obvious that if said scalar value is positive, then air-sample in said sample tube 104 is seen moving out of said sample tube 104; if said scalar value is negative then said sample tube 104 air-sample flow is into said sample tube 104; following the law of cosines.

NOTE: with said small sample fan 107, a negative scalar value is understood to represent forward operation of said sample fan 107. Positive pressure is understood to represent reverse (backward) operation of said sample fan 107: relating to FIGS. 6 & 7.

Ergo, the present invention's novelty and important feature of having a small sample fan 107, turned on by the system's microcontroller 124; should be obvious to anyone steeped in the art to be the means of supplying an air-sample $p_o$ (200) from said system duct-work 102. Further the forced-air sample 109 is siphoned, by forward fan action means, into the internal venturi 10 and focused and forced through said internal venturi's nozzle 111 as shown in FIG. 6 and makes contact with said CO sensor 120.

An example of the present invention's novel capability of using a small air-sample fan 107, which is detailed in FIG. 7 is realised. The captured air-sample 109 in FIG. 7 is guided and directed through the fan structure 107, by fan blades 108 during the time that said system microcontroller 124 as shown in FIG. 6, is operating in a monitoring and interrogating mode. Said CO detector system means of the present invention, periodically turns on said sample fan 107 to capture a small instant sample of air emanating from said duct-work 102 that is passed over said CO sensor 120 and interpreted as a digital electronic signal by interface circuitry 123 in FIG. 6, which in turn is registered and stored in said microcontroller circuit 124 for analysis. If any detected levels of carbon monoxide are present, said microcontroller circuit 124 triggers an alarm and annunciates to all occupants of any home or edifice where said present invention is installed. Instantly, an annunciation alarm and heating system "shut down" or "fail-safe" mode will be instituted in effect Further, it should be obvious to anyone steeped in the art that said CO sensor, which is a special hybrid integrated circuit chip and is readily available off-the-shelf has an operating temperature range and at times the temperature of said duct-work air may reach levels near the maximum operating temperature of said CO sensor. Thus another novel feature of said present invention means, is for said system microcontroller algorithms to quickly take air-samples of the duct-work air periodically; by turning on and off said small sample fan 107. Another command feature of said microcontroller algorithm is to reverse the directional rotation of said sample fan 107 to exhaust out the sampled captured duct-work air sample, to insure that the operating temperature of said CO sensor is maintained within its safe nominal temperature range.

The above theory of operation exists with a minimum operational component system 325 that incorporates a perpendicular insert sample tube 104 amongst its list of components, as shown in FIG. 7 and other figures contained within. Thus it should be obvious to anyone steeped in the art that another novelty of said present invention is for the novel inclusion of a right angle sample tube 104 snap-on extension 121. The right angle extension 121 is affixed to said sample tube 104 at juncture 122 as shown in FIG. 8 as well as FIG. 9 for referencing and illustration. Said right angle extension 121, affixed to sample tube 104 at juncture 122 exists with the advantageous novel feature of 360° rotation to accommodate any preferred angle that will most efficiently collect the maximum amount of duct-work air samples over the minimum period of time.

The capture of air samples 105 from said furnace duct-work is shown in FIG. 9 and its inherent scooping effect is for optimal air sample collection. Thus even during a condition when said furnace system blower fan is off, which is between periods of heated air generated from said burner or boiler system, the lingering of toxic carbon monoxide may remain present and detectable in said system duct-work. Further it is another novel feature of said present invention to periodically monitor and interrogate for the presence of toxic carbon monoxide and if finding any presence of carbon monoxide will annunciate, by audible alarm, to all occupants of a given home or edifice.

OBJECTS OF THE INVENTION

It is the intention of the present invention to teach that a novel alternative approach to the distribution of multi-detector placement throughout a home or edifice, can be simplified and reduced in the number of detectors required.

This novel approach of the present invention is to offer a microcontroller based method means; for completely controlling the periodic and constant interrogation for the presence of carbon monoxide at the source of the carbon monoxide, which is from the burner itself.

An additional novelty of the present invention is for placing the carbon monoxide detection method means as close to the burner or boiler as possible. For it should be obvious to anyone steeped in the art, that the burner or boiler is the prime source of carbon monoxide that is mixed with the hot air and distributed, by way a circulating duct means, to all rooms throughout a home or edifice. It should further be obvious to anyone steeped in the art that if a carbon monoxide detector method means of the present invention is placed at said burner or boiler source, the effectiveness and "assured safety" associated with the present invention CO detector method means is optimized. The present invention is novel for the instant furnace burner or boiler heater shut down and annunciate to all occupants that carbon monoxide is detected. Another novelty of the present invention is its wireless feature that can send wireless data to remote receivers, such as personal computers incorporated into a more complex scheme for home or commercial use. Further it should be obvious to anyone steeped in the art that the present invention, with a novel feature of having its placement at the burner or boiler source, reduces the number of prior art room CO detectors to zero. The present invention is the only method means necessary for an optimized CO detection system. Another intention of the present invention is to use a novel priority algorithm that controls air samples emanating from the forced-air duct-work to enter by way of a small internally mounted controller fan that blows air across a carbon monoxide sensor mounted at the fan venturi outlet. This intention is for instantly collecting an air sample from the duct-work whether the main furnace fan is on or off. Making possible to do periodic and constant monitoring, interrogation and annunciation upon detection of carbon monoxide.

It is another feature of said present invention to have its microcontroller algorithm reverses the directional rotation of said sample fan to exhaust out the sampled captured ductwork air sample, to insure that the operating temperature of said CO sensor is maintained within its safe nominal temperature range.

The overall intentions of this present invention remains to provide maximum safety to the consumer and institute instant shut down of a furnace burner or boiler mechanism, to immediately alleviate the danger of toxic carbon monoxide and to report by audible annunciation, an alert for the consumer.

DETAILED DESCRIPTION OF THE DRAWINGS

Figure 1:
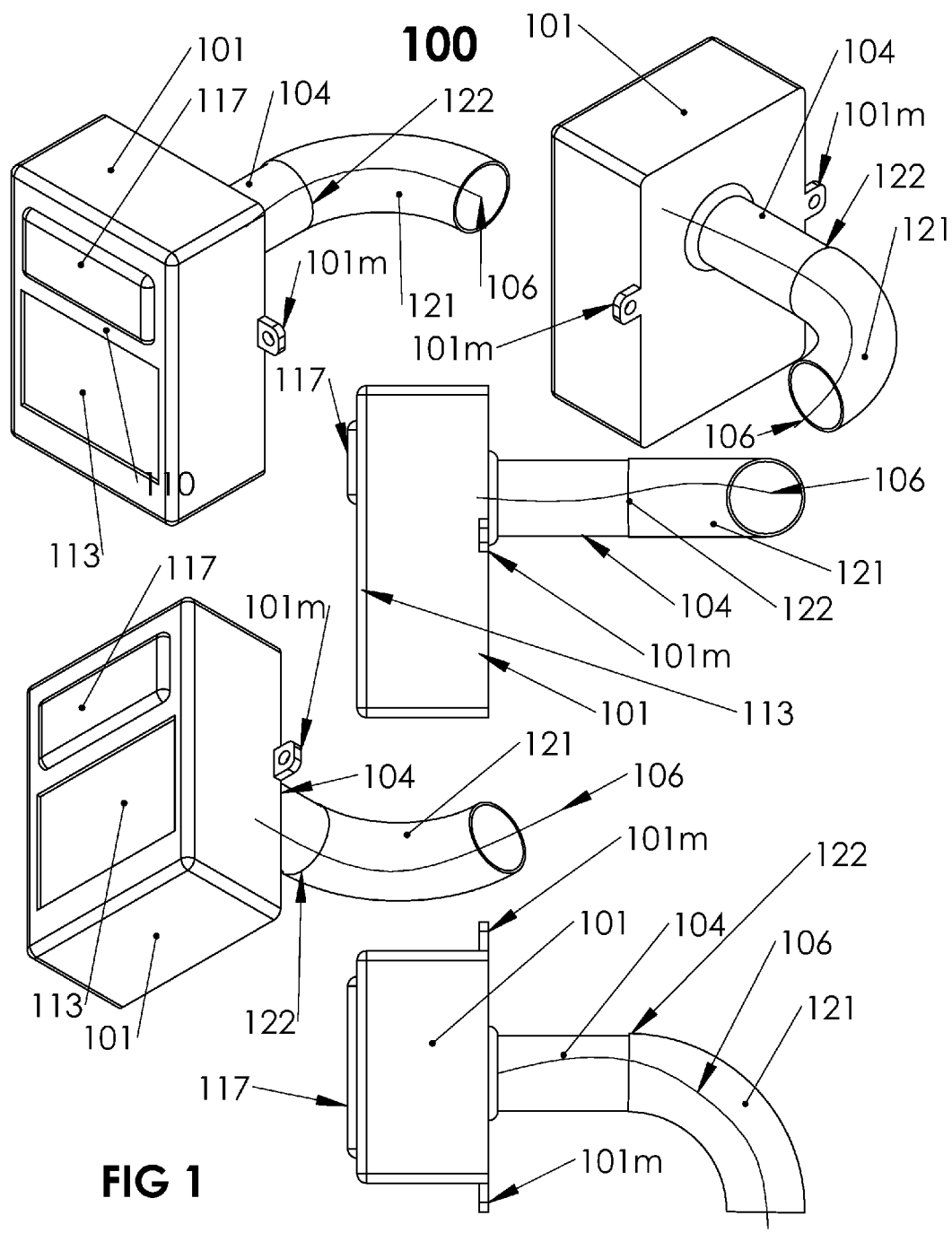
FIG. 1, one of the embodiments of said present invention 100.

FIG. 1, is one of the embodiments of said present invention 100.

Figure 1A:
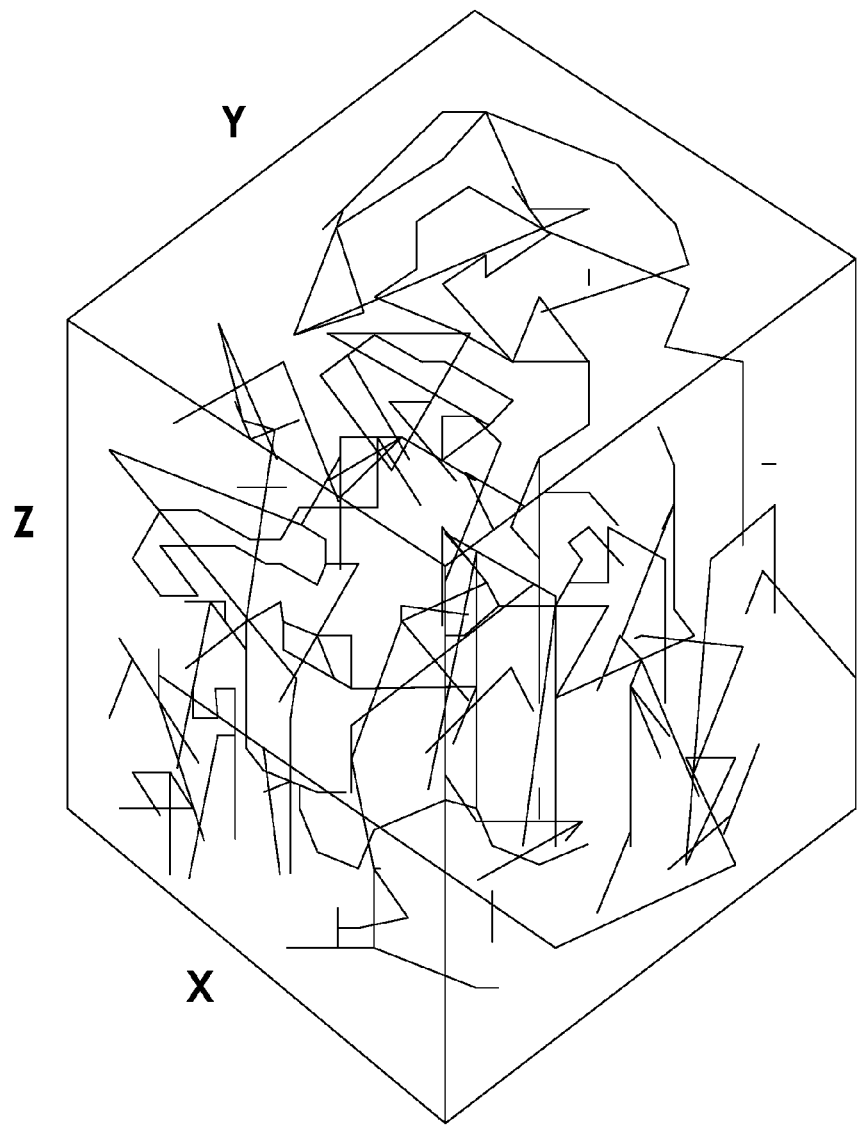
FIG. 1A, a 3D graphic of Brownian Movement of a gas.

FIG. 1A, shows a three dimensional graphic representation of a typical gaseous path caused and taken by Brownian Movement influence. Academically, Brownian Movement is responsible for the permeation of any gas throughout a three dimensional volume by the interaction of gas molecules and dust particles and exists as an ongoing ambient converse process.

Figure 2:
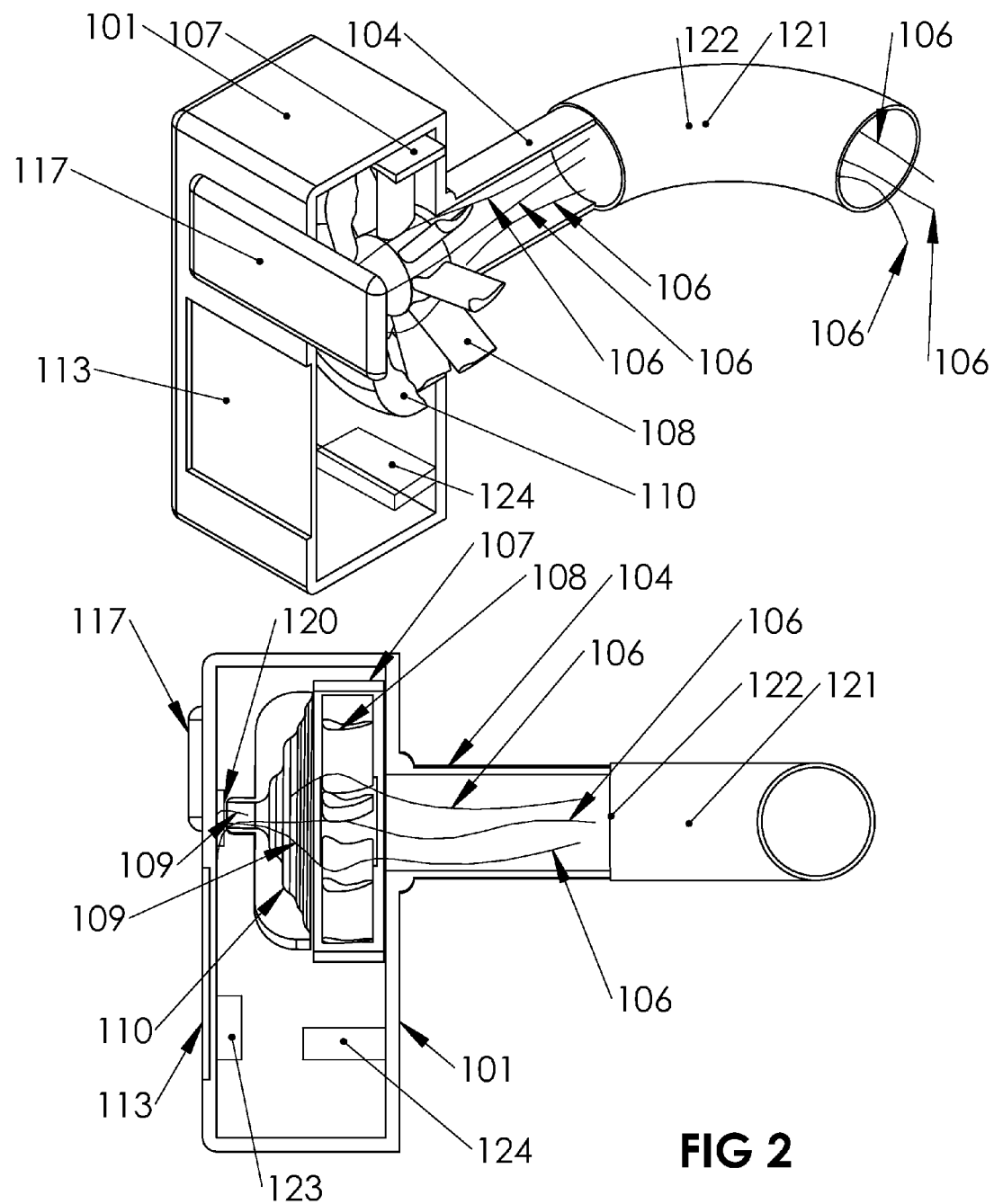
FIG. 2, a basic cutaway right side view of the present invention.

FIG. 2, is a side cutaway view of the present invention enclosure 101 with internal working components and typical sampled air flow 106 emanating from a typical section of duct-work 102 (not shown in this figure; refer to FIGS. 3, 7, & 9), where the present invention is installed and said air sample is directed 106 into said fan structure 107 velocity amplified by fan blades 108 and redirected through internal venturi 110 and nozzle 111 to exist in contact with said CO sensor 120.

Figure 3:
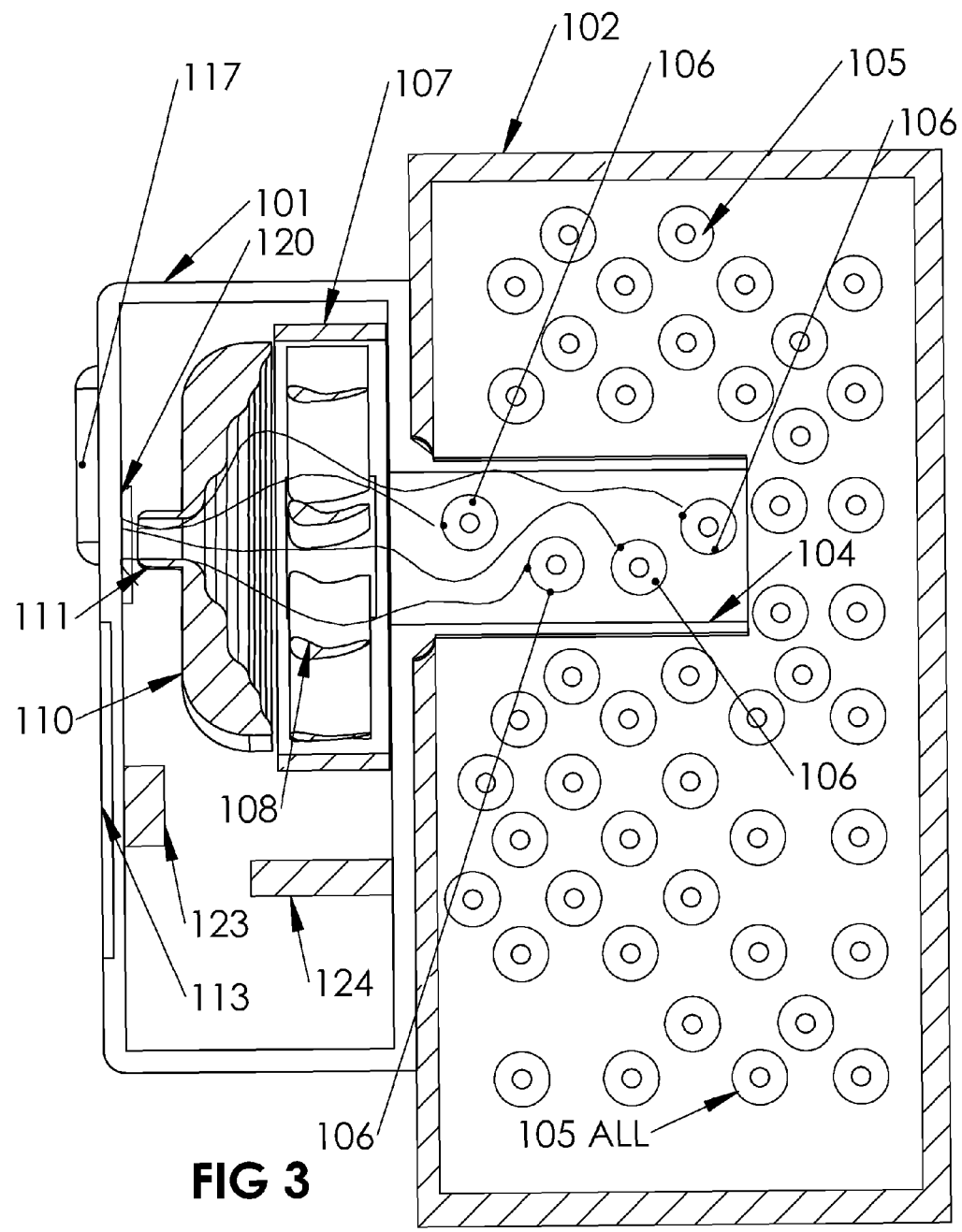
FIG. 3, a right side cutaway view of the present invention inserted into a furnace duct-work section.

FIG. 3, is an illustration of the present invention installed in a section of a typical furnace duct-work system 102, where furnace system forced air 105 is represented by the plus signs and is to be understood as air flowing into the paper. As air 106 is vented into said vent tube 104 it is passed onward to said fan structure 107 where said air-sample 109 is velocity amplified and passes through internal venturi 110 and nozzle 111 to said CO sensor 120 for transduction into a viable electrical signal to be analyzed by said micro-controller circuit 124 after being conditioned by signal processor circuit 123.

Figure 4:
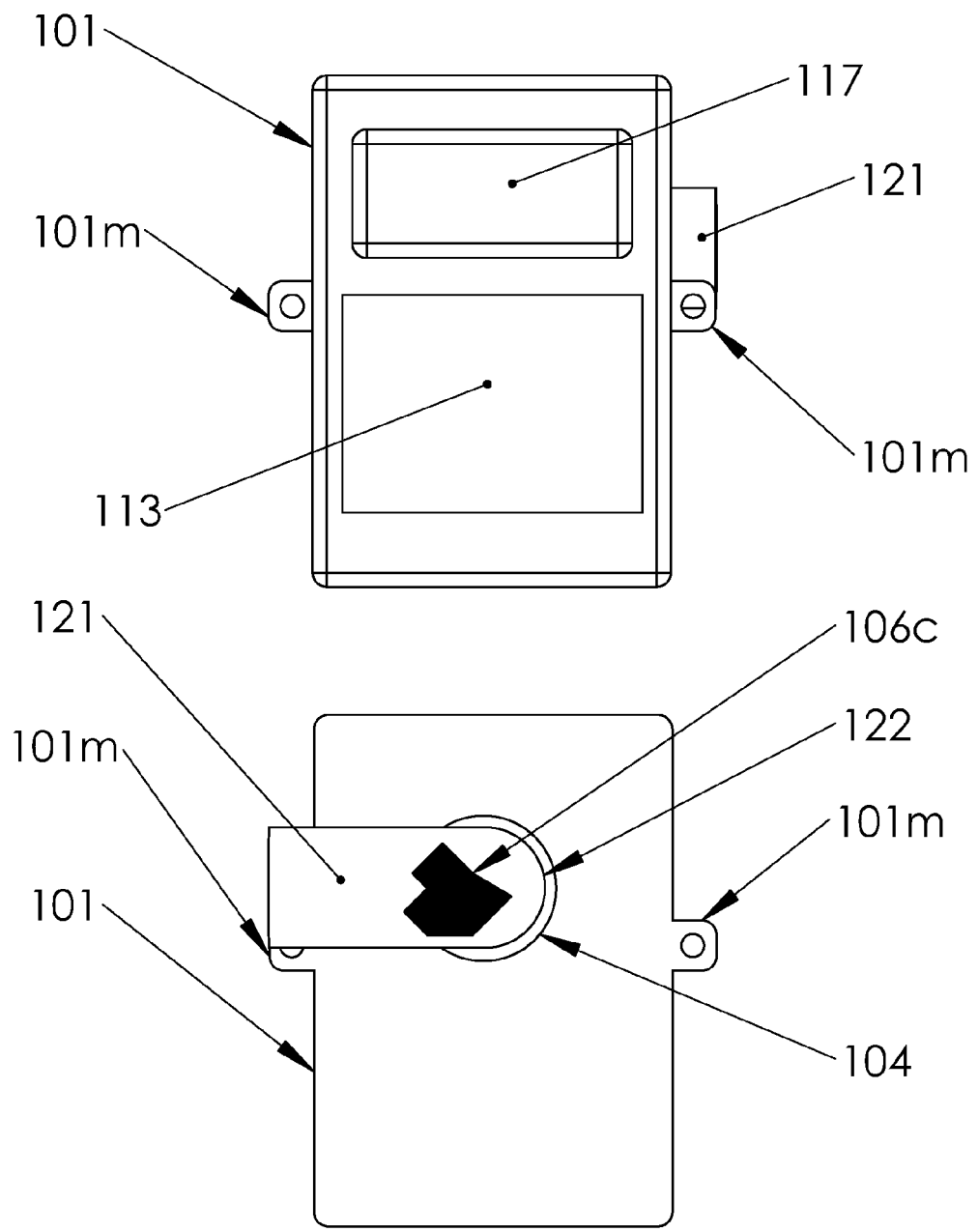
FIG. 4, a rear view of the present invention.

FIG. 4, is a dual graphic showing the front and back views of the present invention.

An overview of said invention's enclosure 101 front view has a windowed display 117 that is a visual method means of display data for user information. Area 113 of said enclosure 101 is the location of various control features such as flat touch sensitive switch data entry. Further mounting tabs 101m are responsible for securing said enclosure 101 to a furnace duct section. Protruding from the enclosure rear is said right angle air-sample rotatable scoop tube 121. Further said back view section shows another view of right angle air-sample rotatable scoop tube 121 and is rotatable around 360° around vent tube 104 at juncture 122. A cutaway view of opening 106h for air-sample flow is seen.

Figure 5:
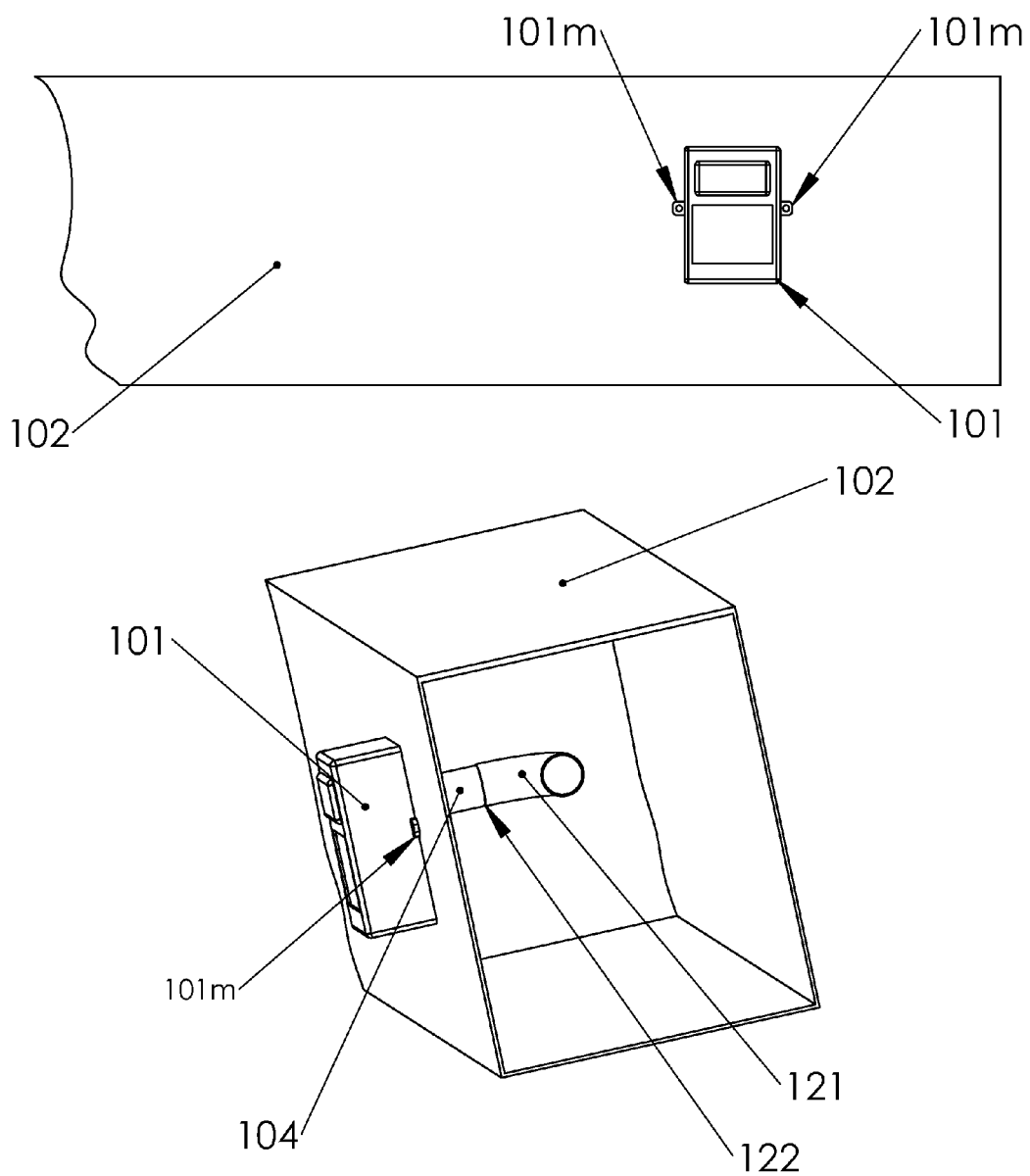
FIG. 5, the present invention mounted to a side section of a typical furnace duct-work; also showing air flow in duct-work section.

FIG. 5, is a dual graphic representation showing the present invention's enclosure 101 installed in a typical section of furnace duct-work 102. Mounting of said present invention's enclosure 101 is simply accomplished by inserting two screws into mounting tabs 101m of said enclosure 101 to said furnace duct-work section 102. Another sectional view of FIG. 5 shows how said rotatable right angle scoop tube 121 can be rotated around vent tube 104 at juncture 122 to enable the optimum amount of air-sample collection flowing inside of duct 102.

Figure 6:
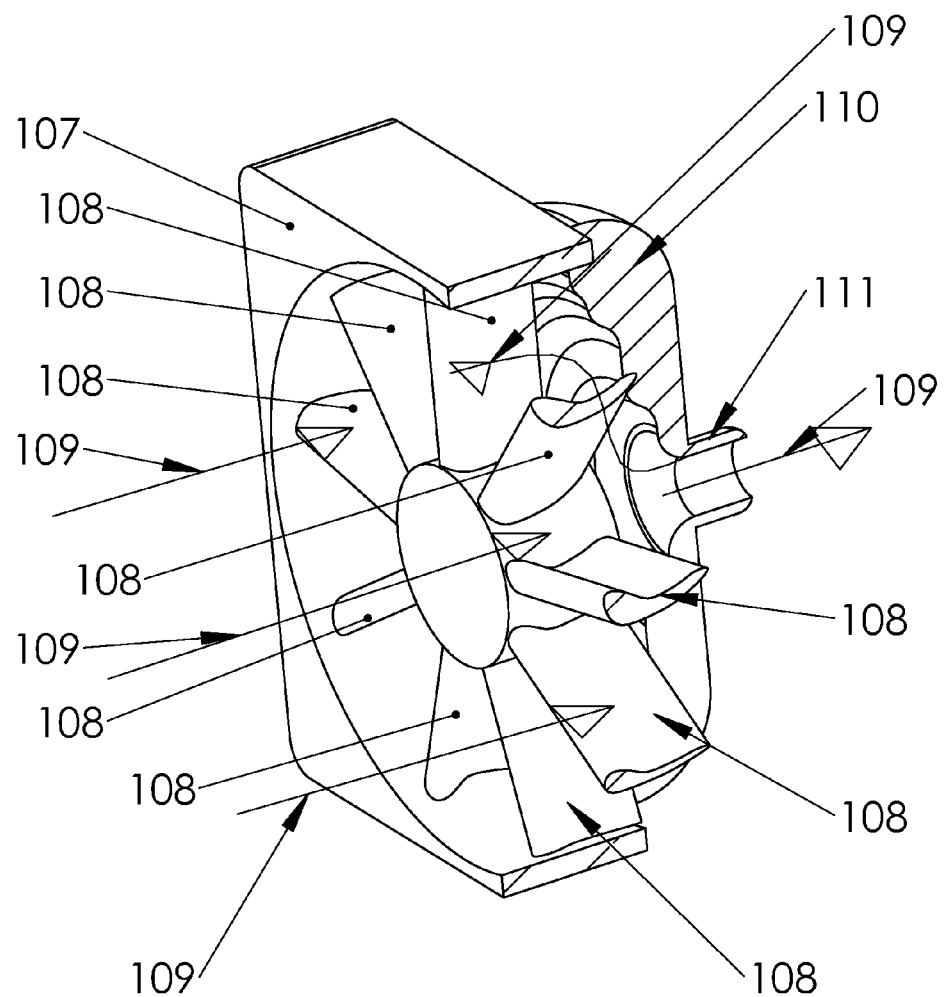
FIG. 6, a cutaway right side view showing key pressure points within the duct and present invention.

FIG. 6, Is a drawing showing three key points of within said furnace duct system $p_d$, nominal intrinsic atmospheric pressure $p_i$, and pressure $p_o$ at or near said CO sensor 120. Said furnace duct system pressure $p_d$ is present in said duct section 102 either when said furnace system blower fan is on or off. When said furnace system blower fan is off, said pressure pd is at atmospheric pressure, which is also the intrinsic pressure of $p_i$; when said furnace system blower fan is on, said pressure $p_d$ is lower than that of atmospheric pressure due to the Venturi principle, which applies as when the velocity of duct air is greater than zero during the high velocity movement of air throughout said furnace duct system. The establishment of this resulting pressure differential ($p_d$–$p_i$), through the action of duct air movement or absence thereof, is seen mathematically as positive or negative around a reference value of atmospheric pressure. This is important observational information that enhances and justifies the novelty of the present invention's capability of extracting periodic air-samples from said duct-work for assurance of immediate analysis and action based upon said analysis to protect occupants of any home or edifice where the present invention is installed and maintained as the CO detection security system.

Figure 7:
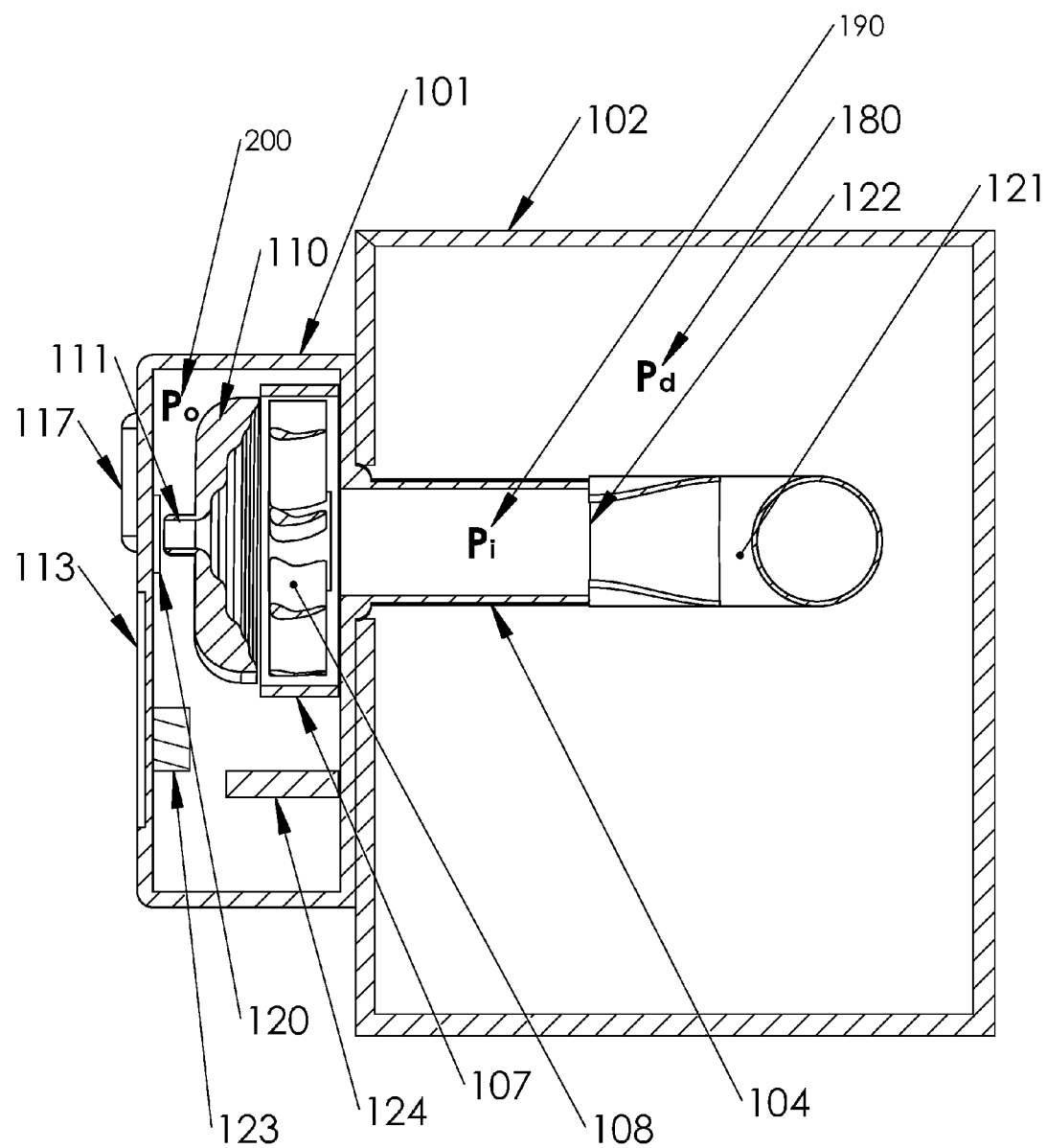
FIG. 7, right side view of the fan and internal venturi mechanism.

FIG. 7, Shows the present invention's internal fan structure and illustrates the directional flow and guidance of said air-samples 109 from a typical furnace duct system through said present invention's internal fan structure 107 and velocity amplified by fan blades 108. Said velocity amplified air-sample is pushed through internal venturi 110 and nozzle 111 to be on contact, for analysis, with said CO sensor, known as component #120, and shown in previous figures in this document.

Figure 8:
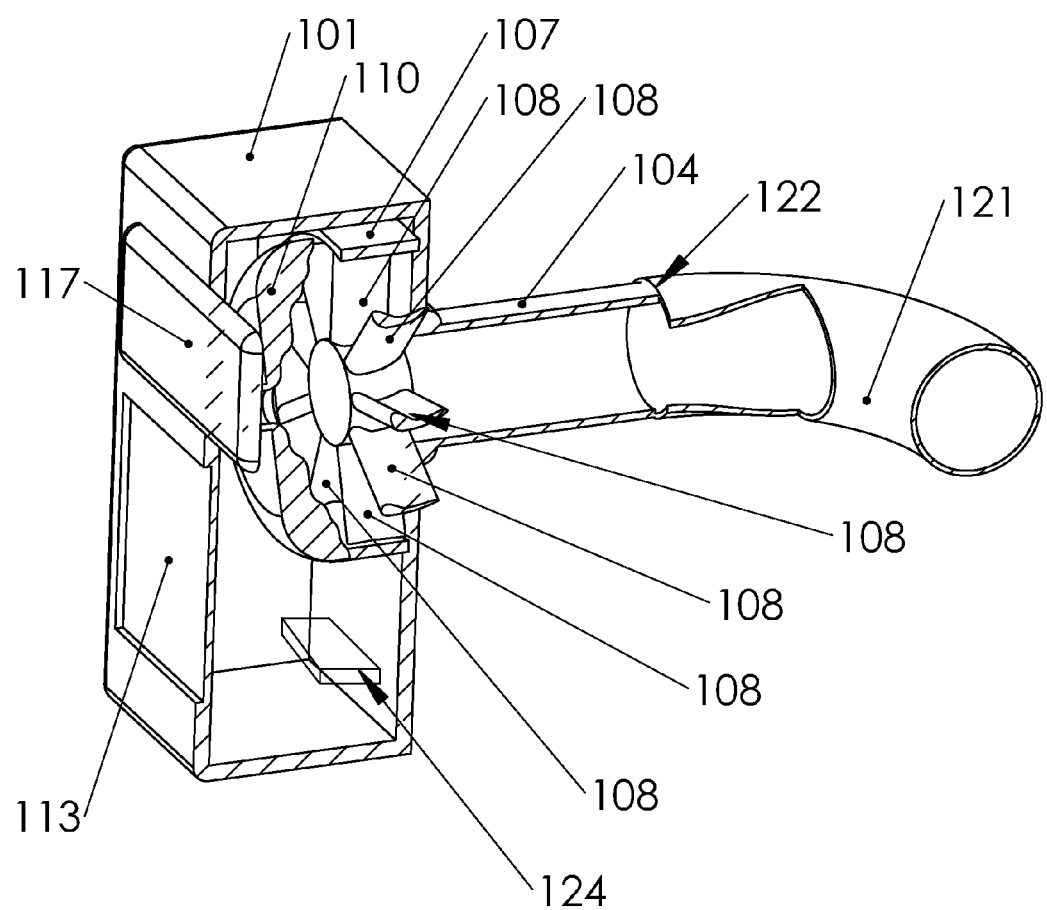
FIG. 8, a top cutaway view of the present invention housing and interior fan, venturi, and right angle cannula.

FIG. 8, the top cutaway view of said present invention is illustrated and exposes the simple and effective path for an air-sample to be guided efficiently, by the novelty of said present invention, to said CO sensor for analysis.

Figure 9:
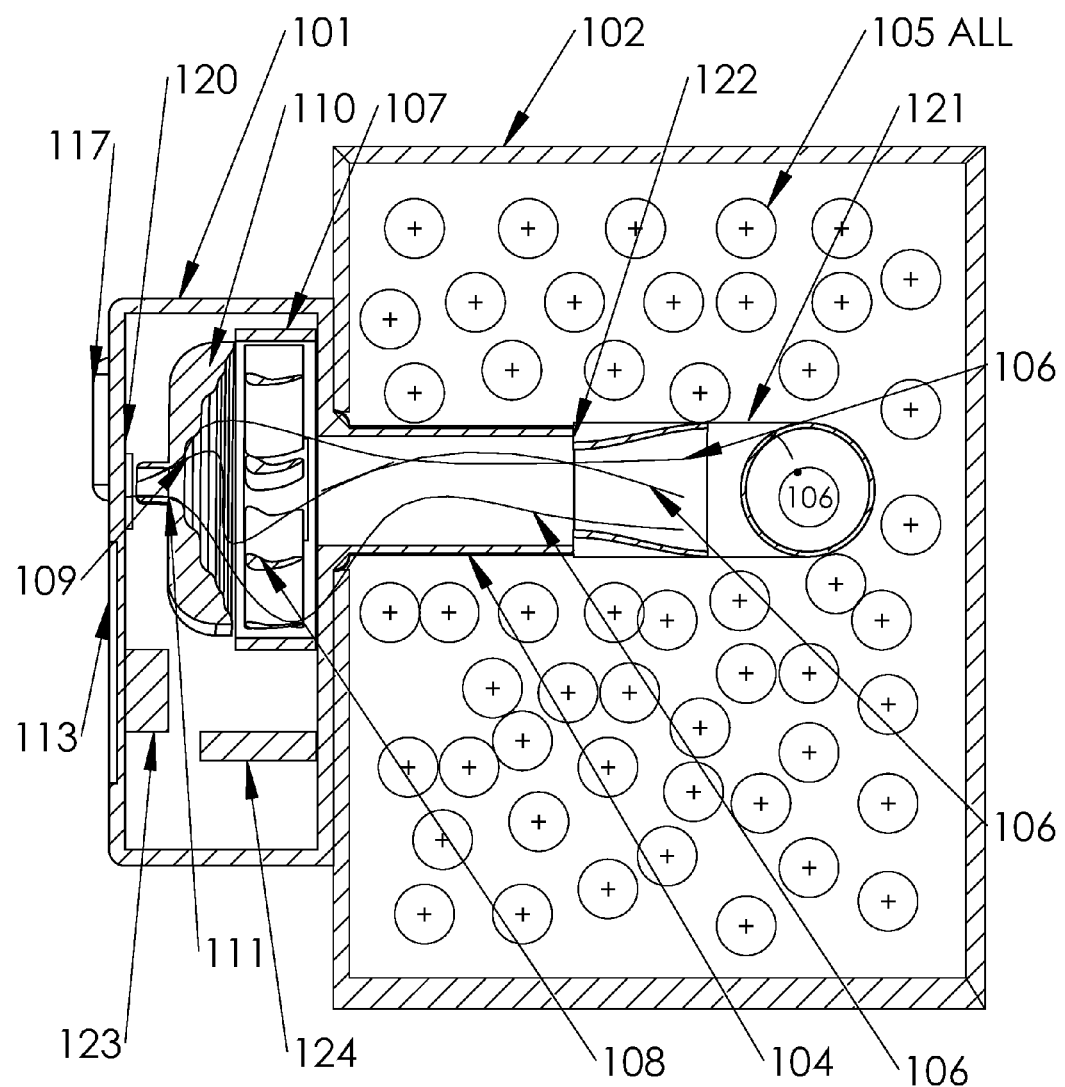
FIG. 9, a side cutaway view of the CO detector system installed in a duct-work section; also showing air flow in duct-work.

FIG. 9, shows a side cutaway view of said present invention that is installed in a typical furnace system duct section 102. Cutaway view includes the rotatable right angle scoop tube 121, which is rotatable around juncture 122 to dynamically connect said right angle tube 121 to straight tube section 104. Said air-sample flow 109 is easily and instantly guided through the present invention. This further illustrates the novelty of said present invention.

The present invention has been described in an illustrated manner and it is to be understood that the terminology, which has been used is intended to be used in the nature of words of description rather than of limitation. Obviously many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. A toxic gas detector, comprising:
   a) ductwork;
   b) an enclosure;
   c) a toxic gas sensor;
   d) an air sample fan; and
   e) a venturi;
   wherein said ductwork communicates with a potential toxic gas heating source of a forced hot air heating system;
   wherein said enclosure is attached directly to, and communicates with, said ductwork, and is disposed directly adjacent to said potential toxic gas heating source of said forced hot air heating system;
   wherein said toxic gas sensor is disposed in said enclosure, communicates with said ductwork, and is disposed directly adjacent to said potential toxic gas heating source of said forced hot air heating system so as to allow said toxic gas sensor to detect a toxic gas at said potential toxic gas heating source of said forced hot air heating system before the toxic gas has a chance to be distributed through said ductwork and infiltrate outlets of said ductwork, and when said toxic gas sensor detects the toxic gas at said potential toxic gas heating source of said forced hot air heating system, said toxic gas detector automatically shuts down said potential toxic gas heating source of said forced hot air heating system;
   wherein said air sample fan is disposed within said enclosure;
   wherein said air sample fan maximizes collection of the toxic gas from said ductwork for detection;
   wherein said venturi is disposed within said enclosure;
   wherein said venturi accelerates the toxic gas in said ductwork to said toxic gas sensor so as to provide accelerated detection of the toxic gas from said ductwork; and
   wherein said air sample fan is reversible between forward and reverse and vise versa for changing direction of the toxic gas from said ductwork.

2. The toxic gas detector of claim 1, further comprising: a straight air sample collection tube.

3. The toxic gas detector of claim 2, wherein said air sample fan is in fluid communication between said straight air sample collection tube and said venturi.

4. The toxic gas detector of claim 2, further comprising a command control.

5. The toxic gas detector of claim 4, wherein said command control is disposed within said enclosure.

6. The toxic gas detector of claim 4, wherein said command control controls direction of rotation of said air sample fan between forward and reverse and vice versa for changing direction of the toxic gas from said ductwork to exhaust out the toxic gas to ensure that operating temperature of said toxic gas sensor is maintained within a safe normal temperature range.

7. The toxic gas detector of claim 1, further comprising mounting tabs.

8. The toxic gas detector of claim 7, wherein said mounting tabs are disposed on said enclosure; and wherein said mounting tabs attach said enclosure to said ductwork.

9. The toxic gas detector of claim 1, further comprising a data entry control panel.

10. The toxic gas detector of claim 9, wherein said data entry control panel is disposed on said enclosure.

11. The toxic gas detector of claim 1, further comprising a remote control; and wherein said remote control is for data entry from a remote location.

12. The toxic gas detector of claim 1, further comprising an alarm to annunciate to all occupants that the toxic gas is detected for providing maximum safety to occupants.

13. The toxic gas detector of claim 1, wherein said potential toxic gas heating source of said forced hot air heating system has a power source; and
   wherein said toxic gas detector is powered by said power source of said potential toxic gas heating source of said forced hot air heating system so as to eliminate a need for batteries to power said toxic gas detector and so as to eliminate a need to detect the toxic gas when said power source of said potential toxic gas heating source of said forced hot air heating system is deactivated.

14. The toxic gas detector of claim 1, further comprising a shutdown/fail-safe mode; and
   wherein said shutdown/fail-safe mode is instituted upon detection of the toxic gas from said ductwork and shutting down said potential toxic gas heating source of said forced hot air heating system.

15. The toxic gas detector of claim 2, further comprising a nozzle; and
   wherein said nozzle accelerates the toxic gas sample from said ductwork to said toxic gas sensor so as to provide accelerated detection of the toxic gas from said ductwork.

16. The toxic gas detector of claim 15, wherein said nozzle is disposed in said enclosure.

17. The toxic gas detector of claim 16, wherein said nozzle extends from said venturi.

18. The toxic gas detector of claim 15, wherein said nozzle is in communication with said venturi.

19. The toxic gas detector of claim 1, further comprising a wireless transfer device; and
   wherein said wireless transfer device is for wirelessly transferring data to and from another wireless communication device.

20. The toxic gas detector of claim 19, wherein said wireless transfer device is disposed within said enclosure.

21. The toxic gas detector of claim 3, wherein said straight air sample collection tube extends from said enclosure and into said ductwork to receive the toxic gas from said ductwork.

22. The toxic gas detector of claim 3, further comprising a right angle elbow air sample collection tube.

23. The toxic gas detector of claim 22, wherein said right angle elbow air sample collection tube is disposed on said straight air sample collection tube; and
   wherein said right angle elbow air sample collection tube extends into said ductwork to receive the toxic gas from said ductwork.

24. The toxic gas detector of claim 22, wherein said right angle elbow air sample collection tube is snappingly disposed on said straight air sample collection tube.

25. The toxic gas detector of claim 22, wherein said right angle elbow air sample collection tube is rotatable 3600 relative to said straight air sample collection tube to maximize collection of the toxic gas from said ductwork for detection.

26. A method of using a toxic gas detector for detecting a toxic gas in ductwork of a potential toxic gas heating source of a forced hot air heating system, comprising the steps of:
   a) mounting the toxic gas detector to the ductwork of the potential toxic gas heating source of the forced hot air healing system, close to the potential toxic gas heating source of the forced hot air heating system that uses a fan and would be the prime source of the toxic gas;
   b) venting air samples emanating from the ductwork of the potential toxic gas heating source of the forced hot air heating system so as to form vented air samples for assuring immediate analysis and action:
   c) analyzing, by a toxic gas sensor of the toxic gas detector, the vented air samples for presence of the toxic gas: and
   d) shutting down the potential toxic gas healing source of the forced hot air heating system, if the toxic gas is detected;
   further comprising the step of blowing the vented air samples onward to, and through, a fan of the toxic gas detector so as to form velocity amplified air, with the fan allowing the air samples to be sampled whether the fan of the potential toxic gas heating source of the forced hot air heating system is on or is off so as to allow periodic and constant monitoring and interrogation of the air samples even when the fan of the potential toxic gas heating source of the forced hot air heating system is off during which time the air samples that linger in the ductwork of the potential toxic gas heating source of the forced hot air heating system arc monitored and interrogated;
   further comprising the step of reversing directional rotation of the fan to exhaust out the velocity amplified air to ensure that operating temperature of the toxic gas sensor is maintained within a safe nominal temperature range; and
   further comprising the step of guiding and directing the velocity amplified air by the fan into, and through, a venturi so as to form venturied air.

27. The method or claim 26, wherein said mounting step includes mounting an enclosure of the toxic gas detector by inserting two screws into mounting tabs of the enclosure to a side section of the ductwork of the potential toxic gas heating source of the forced hot air heating system.

28. The method of claim 26, wherein said venting step includes venting at periods the air samples emanating from the ductwork of the potential toxic gas heating source of the forced hot air heating system into, and through, a vent tube of the toxic gas detector.

29. The method of claim 28, further comprising the step of cutting out a small circular hole in a side of the ductwork of the potential toxic gas heating source of the forced hot air heating system, close to the potential toxic gas heating source of the forced hot air heating system that would be the prime source of the toxic gas.

30. The method of claim 29, further comprising the step of snapping a right angle tube of the toxic gas detector to the vent tube.

31. The method of claim 30, further comprising the step of rotating the right angle tube about the vent tube up to 3600 to accommodate any preferred angle that most efficiently collects a maximum amount of the air samples from the ductwork of the potential toxic gas heating source of the forced hot air heating system over a minimal amount of time to thereby enable an optimum and maximum amount of air samples from the ductwork of the potential toxic gas heating source of the forced hot air heating system to be sampled and be easily and instantly guided.

32. The method of claim 30, further comprising the step of inserting the vent tube and the right angle tube attached thereto into the small circular hole in the side section of ductwork of the potential toxic gas heating source of the forced hot air heating system, close to the potential toxic gas heating source of the forced hot air heating system so as to eliminate a need for multiple room toxic gas detectors.

33. The method of claim 26, further comprising the step of controlling completely the periods of venting the air samples.

34. The method of claim 26, further comprising the step of focusing and forcing the venturied air by a nozzle of the toxic gas detector onto the toxic gas sensor for transduction into a viable electrical signal to be analyzed by a micro-controller circuit of the toxic gas detector after being conditioned by a signal processor circuit of the toxic gas detector to detect presence of the toxic gas.

35. The method of claim 34, further comprising the step of translating the viable electrical signal by an interface circuit of the toxic gas detector so as to form a translated electrical signal.

36. The method of claim 35, further comprising the step of sending the translated electrical signal to the micro-controller circuit.

37. The method of claim 34, further comprising the step of taking and capturing small instant air samples quickly, by the micro-controller, from the ductwork of the potential toxic gas heating source of the forced hot air heating system by turning the fan on and off periodically.

38. The method of claim 26, further comprising the step of entering, at an input control parameter of the toxic gas detector, adjustments to accommodate the toxic gas sensor being used.

39. The method of claim 34, further comprising the step of displaying in a windowed display of the toxic gas detector data including readings from the micro-controller circuit for user information.

40. The method of claim 26, further comprising the step of sending wireless data to remote receivers including personal computers.

41. The method of claim 26, further comprising the step of sounding an alarm to annunciate to all occupants that the toxic gas is detected for providing maximum safety to all occupants.

* * * * *